United States Patent
Kirihata et al.

(10) Patent No.: US 8,431,738 B2
(45) Date of Patent: Apr. 30, 2013

(54) OPTICALLY ACTIVE α-AMINO ACID INTO WHICH BSH IS INTRODUCED AND METHOD FOR SYNTHESIZING THE SAME

(75) Inventors: Mitsunori Kirihata, Sakai (JP); Tomoyuki Asano, Osaka (JP); Kohki Uehara, Osaka (JP); Yoshihide Hattori, Sakai (JP); Shintaro Kusaka, Sakai (JP)

(73) Assignee: Stella Pharma Corporation, Osaka (JP)

( * ) Notice: Subject to any disclaimer, the term of this patent is extended or adjusted under 35 U.S.C. 154(b) by 123 days.

(21) Appl. No.: 13/055,700

(22) PCT Filed: Jul. 23, 2009

(86) PCT No.: PCT/JP2009/063157
§ 371 (c)(1),
(2), (4) Date: Jan. 24, 2011

(87) PCT Pub. No.: WO2010/010912
PCT Pub. Date: Jan. 28, 2010

(65) Prior Publication Data
US 2011/0124914 A1    May 26, 2011

(30) Foreign Application Priority Data
Jul. 24, 2008    (JP) ................................. 2008-191260

(51) Int. Cl.
C07C 61/12    (2006.01)
C07C 323/53    (2006.01)
C07C 319/20    (2006.01)

(52) U.S. Cl.
USPC .......................................... 562/498; 562/507

(58) Field of Classification Search ........................ None
See application file for complete search history.

(56) References Cited

U.S. PATENT DOCUMENTS
6,017,902 A    1/2000    Glass et al.

FOREIGN PATENT DOCUMENTS
JP    2-85291    3/1990
JP    2008-94730    4/2008

OTHER PUBLICATIONS

Zaragoza Dorwald, Side Reactions in Organic Synthesis, Wiley-VCH Verlag GmbH & Co. KGaA, Weinheim, Preface. p. IX.*
Gibson et al, Drug Metabolism and Disposition, Boron Neutron Capture Therapy of Brain Tumors: Investigation of Urinary Metabolites and Oxidation Products of Sodium Borocaptate by Electrospray Ionization Mass Spectrometry, 2001, 29(12), pp. 1588-1598.*
Extended European Search Report dated Jan. 17, 2012 in corresponding Application No. 09800426.0 in 4 pages.
I. M. Wyzlic, et al.; A General, Convenient Way to Carborane-Containing Amino Acids for Boron Neutron Capture Therapy; Tetrahedron Letters; 33; 7489-7490, 1992.
W. Tjarks, et al.; The use of boron clusters in the rational design or boronated nucleosides for neutron capture therapy of cancer; Chem., 2000, 614-615; 37-47.
Ken-Ichiro Imamura, et al.; Synthesis and in Vitro Evaluation of 5-closo- and 5-nido-Orthocarboranyluridines as Boron Carriers; Bull. Chemical Society of Japan; 1997; 70. 3103-3110.
A. S. Al-Madhorn, et al.; Synthesis of a Small Library . . . ; J. Med. Chem., 2002; 45; 4018-4028.
F. Compostella, et al.; Synthesis of Glycosyl Carboranes with Different Linkers . . . ; Res. Develop. Neutron Capture Ther., 2002, 81-84.
S. B. Kahl, et al.; Progress in Neutron Capture Therapy for Cancer; Plenum Press, New York 1992; 223, 1992.
J. Cai, et al.; Boron-Containing Polyamines as DNA Targeting Agents for Neutron Capture . . . ; J. Med. Chem., 1997; 40; 3887-3896.
H. Lim, et al.; o-Carboranyl Derivatives of 1,3,5-Triazines; Res. Develop. In Neutron Capture Ther., 2002.
I. Slepukhina, et al.; Fragmentation . . . ; Organomet Chem. 690; 2005; 2796-2801.

* cited by examiner

*Primary Examiner* — Paul A Zucker
(74) *Attorney, Agent, or Firm* — Knobbe Martens Olson & Bear LLP

(57) ABSTRACT

Disclosed is the method for producing an optically active BSH amino acid, which comprises a step of reacting an optically active α-amino acid derivative having a halogen in a side chain with a cyanoethyl BSH compound represented by formula (1). An optically active BSH amino acid obtained by the method is also disclosed.

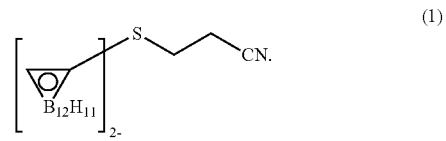

(1)

4 Claims, No Drawings

OPTICALLY ACTIVE α-AMINO ACID INTO WHICH BSH IS INTRODUCED AND METHOD FOR SYNTHESIZING THE SAME

This application is the U.S. National Phase under 35. U.S.C. §371 of International Application PCT/JP2009/063157, filed Jul. 23, 2009, which claims priority to Japanese Patent Application No. 2008-191260, filed Jul. 24, 2008. The International Application was published under PCT Article 21(2) in a language other than English.

TECHNICAL FIELD

The present invention relates to an optically active α-amino acid into which mercaptoundecahydrododecaborate (BSH: borocaptate) is introduced, and a method for synthesizing the same. More specifically, the present invention relates to an optically active α-amino acid into which BSH is introduced, which is particularly useful as a therapeutic agent for neutron capture used in boron neutron capture therapy (BNCT) and a method for synthesizing the same.

BACKGROUND ART

Recently, attention has been drawn to boron neutron capture therapy (BNCT) as a novel cancer therapeutic method utilizing a radioisotope. The boron neutron capture therapy is a therapeutic method in which a boron compound containing boron-10 isotope (10B) is incorporated into cancer cells and the cancer cells are irradiated with low energy neutron (for example, thermal neutron), and thus the cancer cells are locally destroyed by a nuclear reaction which arises in the cells. In this therapeutic method, since it is important to selectively accumulate the boron compound containing 10B in cells of cancerous tissues so as to enhance the therapeutic effect, boron compounds which are selectively incorporated into cancer cells has been developed.

There have been synthesized so far, as a drug used in BNCT, some boron-containing compounds in which boron atoms or boron atomic groups are introduced as a basic skeleton. Examples of the drug used in actual clinical practice include p-boronophenylalanine (BPA) and BSH. Among these drugs, BSH is mainly used for the treatment of brain tumor in the form of a sodium salt, and utility thereof has been confirmed (see, for example, Non-Patent Documents 1 to 8).

On the other hand, it is said that requirements of an amino acid increase so as to assure intracellular metabolism accompanied with abnormal proliferation in cancerous tissues, and that a decrease in selectivity of a membrane transport protein and an increase in a transporting function of an amino acid is accelerated. Therefore, use of an amino acid is one of the options so that a compound may be selectively incorporated into cancer cells. However, there has not yet been reported about BSH into which an optically active α-amino acid with high purity, which is convenient for the incorporation, is introduced.

PRIOR ART DOCUMENTS

Non-Patent Documents

Non-Patent Document 1: I. M. Wyzlic et al., Tetrahedron Lett., 1992, 33, 7489-7490;
Non-Patent Document 2: W. Tjark, J. Organomet. Chem., 2000, 614-615, 37-47;
Non-Patent Document 3: K. Imamura et al., Bull. Chem. Soc. Jpn., 1997, 70. 3103-3110;
Non-Patent Document 4: A. S. Al-Madhorn et al., J. Med. Chem., 2002, 45, 4018-4028;
Non-Patent Document 5: F. Compostella et al., Res. Develop. Neutron Capture Ther., 2002, 81-84;
Non-Patent Document 6: S. B Kahl et al., Progress in Neutron Capture Therapy for Cancer, Plenum Press, New York 1992, 223;
Non-Patent Document 7: J. Cai et al., J. Med. Chem., 1997, 40, 3887-3896;
Non-Patent Document 8: H. Lim et al., Res. Develop. Neutron Capture Ther., 2002, 37-42

SUMMARY OF THE INVENTION

Problems to be Solved by the Invention

It is desired to develop, as a boron compound selectively incorporated into cancer cells which can be utilized for BNCT, a compound which enables quick and accurate accumulation of BSH to a diseased part.

Thus, an object of the present invention is to provide an optically active α-amino acid into which BSH is introduced, and a simple and accurate method for synthesizing the same.

Means for Solving the Problems

The present inventors have intensively studied and, as a result, have found that the above object can be achieved by an optically active α-amino acid into which BSH is introduced, and a method for synthesizing the same shown below, and thus the present invention has been completed.

That is, the present invention provides a method for producing an optically active BSH amino acid, which comprises the step of reacting an optically active α-amino acid derivative having a halogen in a side chain with a cyanoethyl BSH compound represented by the following formula (1):

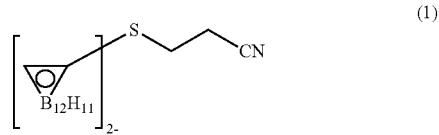

(1)

In the method for producing an optically active BSH amino acid, the halogen is preferably bromine.

In the method for producing an optically active BSH amino acid, the optically active BSH amino acid is preferably in L-form.

The present invention also relates to an optically active BSH amino acid obtained by any one of the production method described above.

The optically active BSH amino acid is preferably in L-form.

The optically active BSH amino acid is preferably a compound represented by the following Chemical Formula (2):

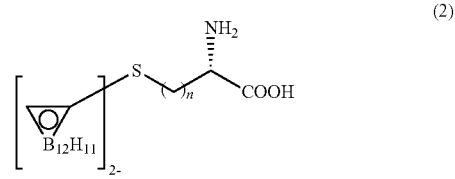

(2)

wherein n represents an integer of from 1 to 6.

Effects of the Invention

It is possible to obtain an optically active BSH amino acid having high purity via very simple pathways by applying the production method of the present invention. Furthermore, it becomes possible to produce an optically active BSH amino acid widely using various kinds of amino acids regardless of the kind of an amino acid. The optically active BSH amino acid having high purity thus obtained is particularly useful for BNCT targeting cancer cells into which an amino acid incorporation is enhanced.

MODES FOR CARRYING OUT THE INVENTION

Embodiments of the present invention will be described below.

In the present description, the "optically active α-amino acid derivative having a halogen in a side chain" includes, in addition to an amino acid derivative in which a halogen is added to a naturally occurring optically active amino acid, amino acid derivatives in which various kinds of amino acids having a side chain, which do not naturally exist, are halogenated. Such an amino acid derivative is represented by the structural formula: $X\text{-}(A)_n\text{-}R\text{—}CH(NH_2)COOH$, and refers to an amino acid derivative in which a coupling manner of an amino group, a carboxyl group or the like to α carbon is any one of optical isomers sterically in D-form or L-form. Herein, X represents one halogen atom selected from the group consisting of a chlorine atom, a bromine atom, an iodine atom and a fluorine atom. A represents a linear alkylene, a branched alkylene or a substituted alkylene, and n represents an integer of from 1 to 10. R may be present or absent and, if present, it represents a linear alkylene, branched alkylene or substituted alkylene having 1 to 6 carbon atoms. Herein, when A and/or R are substituted alkylenes, each separate substituent includes, but is not limited to, one or more kinds of substituents including an amino group, a non-substituted or substituted phenyl group, an aminocarbonyl group, a methylthio group, a group having a heterocycle and a group having a fused heterocycle. Preferably, the "optically active α-amino acid derivative having a halogen in a side chain" is an optically active α-amino acid derivative having a halogen at the end of a side chain. Examples of the preferred optically active α-amino acid derivative include a series of amino acid derivatives in which A is a linear or branched alkylene having 1 to 6 carbon atoms, and R is absent. X is particularly preferably bromine. These amino acid derivatives are particularly preferably in L-form regardless of the kind of the side chain.

The optically active α-amino acid derivative having a halogen in a side chain also includes commercially available ones such as D-/L-bromophenylalanine and D-/L-aminobromobutanoic acid, which can be used as they are in the reaction of the present invention. Alternatively, the optically active α-amino acid derivative can be synthesized from a commercially available compound using a known method. Examples of such a method include, but are not limited to, a method by radical halogenation of a commercially available optically active alkylamino acid, a specific bromination of an optically active amino acid and the like.

Next, a cyanoethyl BSH compound represented by Chemical Formula (1):

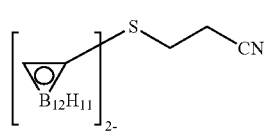

(1)

is not limited, but can be synthesized in accordance with the method known to the document (for example, Gabel, D.; Moller, D.; Harfst, S.; Rosler, J.; Ketz, H.; Inorg. Chem. 1993, 32, 2276-2278). That is, in this method, BSH and β-bromopropionitrile are reacted in acetonitrile, and then the reaction product is treated with tetramethylammonium hydroxide or the like to obtain the objective cyanoethyl BSH compound.

Herein, BSH is a compound having a boron cluster structure of icosahedron including boron, hydrogen and sulfur atoms. BSH has a so-called three center bond structure in which, regardless of an inorganic low molecular compound, the volume is larger than that of the benzene ring and three boron atoms have two electrons in common, and also has a specific structure in which electrons are localized.

In the present description, it may be conveniently represented by the following formula:

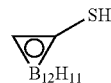

In the present invention, first, a compound in which a cyanoethyl group and an amino acid are added to S of BSH is produced by a coupling reaction of such a cyanoethyl BSH compound and an optically active α-amino acid derivative having a halogen in a side chain. Such a compound is a compound represented by the following formula:

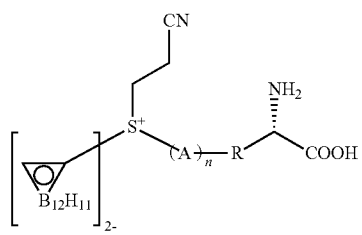

in the case of L-form. The coupling reaction can be performed, for example, by dissolving an optically active α-amino acid derivative having a halogen in a side chain and a cyanoethyl BSH compound in a solvent such as acetonitrile, THF or propionitrile, and reacting under reflux at room temperature to 80° C. for 1 to 72 hours.

In the present invention, the compound represented by Chemical Formula (3) is further treated with tetramethylammonium hydroxide or the like to obtain an optically active BSH amino acid. The reaction can be performed, for example, by dissolving the compound (3) and tetramethylammonium hydroxide in a solvent such as acetone, acetonitrile or propionitrile, and reacting at 0 to 50° C. for 5 minutes to 2 hours.

Each product in each step may be isolated and purified or may be subjected to the subsequent step as it is. The isolation and purification means include washing, extraction, recrystallization methods, various chromatographies and the like. In each product in each step, these isolation and purification means can also be used alone, or in appropriate combination of two or more kinds of them. In the present invention, the reaction can be simply allowed to proceed particularly by omitting the isolation and purification step of the product (3). Even if the reaction is allowed to process in one step as described above, a high-purity optically active BSH amino acid can be obtained with high yield without causing any problem.

Usually, in case where an amino acid is used in the reaction, it is preferred to protect carboxyl and amino groups with high reactivity. Examples of the protection method include, but are not particularly limited to, a method of substituting with a methyl group, an ethyl group, a benzyl group, a t-butyl group or the like in the case of a carboxyl group. Examples of the protection method include a method of substituting with a carbobenzyloxy group, a t-butoxycarbonyl group, a benzoyl group, an acetyl group or the like in the case of an amino group.

Also in the present invention, it is possible to subject to the reaction in a state where the moieties of the carboxyl and amino groups of the optically active α-amino acid derivative having a halogen in a side chain are protected with known protective groups. However, in order to avoid an undesired influence such as the occurrence of racemization in the deprotection reaction, and a decrease in yield caused thereby, it is more preferred to omit addition and deprotection of a protective group. It becomes apparent that, in the reaction of the present invention, the reaction conveniently proceeds at the moieties of the carboxyl and amino groups of the optically active α-amino acid derivative even in a non-protected state. In case where a non-protected amino acid derivative is used in the reaction, the deprotection process leading to racemization can be omitted and an optically active BSH amino acid derivative can be obtained with accuracy.

The thus obtained optically active BSH amino acid derivative of the present invention can be obtained as various kinds of amino acid derivatives containing BSH added optionally by varying the kind of the optically active amino acid having a halogen in a side chain, which is used as a starting substance. Such a compound includes a BSH amino acid in L-form represented by the formula:

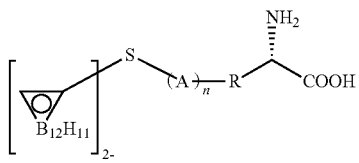

wherein A and R are as defined above.

Among these, preferably preferred is a BSH amino acid in L-form represented by the formula:

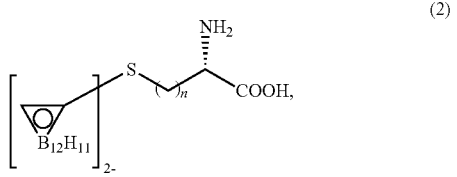

(2)

but is not limited thereto.

Such a compound can be suitably used as it is, or used in the form of a pharmaceutically acceptable salt, or used in the form of a pharmaceutical preparation known to a person with an ordinary skill in the art by mixing them with a pharmaceutically acceptable carrier, or used in the form of a BSH-enclosed viral envelope vector in a boron neutron capture therapy (BNCT). Examples of the pharmaceutically acceptable salt include salts with an inorganic base, salts with an organic base, salts with an inorganic acid, salts with an organic acid, salts with a basic or acidic amino acid and the like. Preferred examples of the salts with an inorganic base include alkali metal salts such as a sodium salt and a potassium salt; alkali earth metal salts such as a calcium salt and a magnesium salt; an aluminum salt, an ammonium salt and the like. Preferred examples of the salts with an organic base include salts with trimethylamine, triethylamine, pyridine, picoline, ethanolamine, diethanolamine, triethanolamine, dicyclohexylamine, N,N'-dibenzylethylenediamine and the like. Preferred examples of the salts with an inorganic acid include salts with hydrochloric acid, hydrobromic acid, nitric acid, sulfuric acid, phosphoric acid and the like. Preferred examples of the salts with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferred examples of the salts with a basic amino acid include salts with arginine, lysin, ornithine and the like. Preferred examples of the salts with an acidic amino acid include salts with aspartic acid, glutamic acid and the like The treatment is performed via any appropriate route of administration by administrating a drug containing the compound of the present invention using a method in which the compound is accumulated at the target site. The compound of the present invention is preferably concentrated to tumor. The pharmaceutical preparation containing the compound can be administered at a time, or can be sequentially administered. Administration of the pharmaceutical preparation can be optionally repeated. If desired, after removing the tumor to a surgically possible extent, the remaining tumor can also be destroyed using the pharmaceutical preparation of the present invention.

The treatment using the BSH amino acid pharmaceutical preparation of the present invention is performed via any appropriate route of administration by administering using a method in which a BSH amino acid is accumulated in the target tumor. The BSH amino acid is preferably concentrated to the tumor before irradiation with radiation. A tumor/blood ratio before irradiation with radiation is advantageously about 2:1 or at least 1.5:1. The BSH amino acid can be administered at a time, or can be sequentially administered. After the compound is desirably accumulated in the tumor, the site is irradiated with an effective amount of low energy neutron. The site can be irradiated through the skin, or the site can be completely or partially exposed before irradiation. Administration of the BSH amino acid and the subsequent irradiation with radiation can be optionally repeated. If desired, after removing the tumor to a surgically possible extent, the remaining tumor is destroyed using the BSH amino acid of the present invention. In another aspect, a proper amount of the BSH amino acid may be administered to patients, followed by irradiation with an effective amount of Californium-252 which is a naturally occurring neutron radiation substance. It is preferred that Californium-252 is inserted into the tumor and then removed within a proper time.

In order to administer the BSH amino acid of the present invention, the BSH amino acid can be administered to patients by mixing with proper excipients, adjuvants and/or pharmaceutically acceptable carriers, alone or using in combination with other drugs. The carriers which can be particularly preferably used include, but are not limited to, physiological saline, buffered physiological saline, dextrose, water and the like. In an embodiment of the present invention, the pharmaceutically acceptable carriers are pharmaceutically inactive.

The BSH amino acid of the present invention is administered orally and parenterally. In the case of parenteral administration, the BSH amino acid can be administered intraarterially (for example, via carotid artery), intramuscularly, subcutaneously, intramedullary, intrathecally, intraventricularly, intravenously, intraperitoneally, or intranasally.

The pharmaceutical preparation can be formulated into any form such as powders, granules, fine grain agents, dry syrups, tablets, capsules, injections and liquids. According to the dosage form, using a pharmaceutically known technique, the pharmaceutical preparation can be prepared by appropriately mixing with, or diluting and dissolving together with pharmaceutical additives, for example, proper excipients; disintegrants; binders; lubricants; diluents; buffers such as organic acids including phosphoric acid, citric acid, succinic acid, acetic acid and other organic acids, or salts thereof; isotonizing agents; antiseptics; humectants; emulsifiers; dispersing agents; stabilizers; solubilizers; antioxidants such as ascorbic acid; low molecular (less than about 10 residues) polypeptides (for example, polyarginine or tripeptides); proteins (for example, serum albumin, gelatin, or immunoglobulin); hydrophilic polymers (for example, polyvinyl pyrrolidone); amino acids (for example, glycine, glutamic acid, aspartic acid, or arginine); monosaccharides, disaccharides and other carbohydrates (including cellulose or derivatives thereof, glucose, mannose, or dextrin); chelating agents (for example, EDTA); sugar alcohols (for example, mannitol or sorbitol); counter ions (for example, sodium); and/or nonionic surfactants (for example, polysolvate, poloxamer). Such a substance, which enhances isotonicity and chemical stability, is nontoxic to the recipient in the dose and concentration used.

Technologies for formulation and administration are described, for example, in the latest edition and the latest supplement of Japanese pharmacopoeia, and the final edition of "REMINGTON'S PHARMACEUTICAL SCIENCES" (Maack Publishing Co., Easton, Pa.).

A pharmaceutical preparation of the BSH amino acid of the present invention is a drug in which the objective drug is contained in an effective amount for achieving the object, and a "therapeutically effective amount" or a "pharmaceutically effective amount" refers to the amount of the drug, which is sufficiently recognized by a person with an ordinary skill in the art and is effective to exert the pharmaceutical effect. Determination of a therapeutically effective dose is sufficiently known to a person with an ordinary skill in the art.

A therapeutically effective amount refers to the amount of the drug that alleviates the condition of a disease by administration. Therapeutic efficacy and toxicity of such compounds can be determined by standard pharmaceutical procedures in cell cultures or experimental animals. The dose is preferably within a range of the circulating concentration including ED50 with little or no toxicity. This dose may vary within this range depending upon the dosage form used, sensitivity of patients, and the route of administration. As an example, the dose of the composite is appropriately selected according to ages and other conditions of patients, kinds of diseases, kind of composites used and the like.

Specific examples of the production of the optically active BSH amino acid of the present invention will be described by way of aspects of examples, but the present invention is not limited thereto.

EXAMPLE (Production of Starting Substance)

In the following examples, analysis and isolation and purification of a compound were performed using the following models and reagents.

NMR spectrum: JEOL JMTC-400/54/SS 400 MHz (manufactured by JEOL, Ltd.). Unless otherwise specified, TMS was used as an internal standard. The following chemical shift was expressed by the δ value.

Silica gel for column chromatography: BW-200 (manufactured by FUJI SILYSIA CHEMICAL LTD.)

(a) Preparation of 2-amino-4-bromobutanoic acid in L-Form

A commercially available (S)-(+)-2-amino-4-bromobutyric acid hydrobromide (manufactured by TOKYO KASEI KOGYO CO., LTD.) was purchased and used.

(b) Preparation of Bromo Addition Alanine in L-Form

This compound was prepared with reference to the method described in Org. Biomol. Chem., 2005, 3, 2476-2481.

Under ice cooling, 10 g of L-serine was dissolved in 200 ml of 1N NaOH and 20.9 g of $(Boc)_2O/100$ ml (1 eq) of dioxane were added dropwise, and the mixture was stirred for 30 minutes and, after returning to room temperature, the mixture was stirred for 6 hours.

Using a liquid separation operation, the unreacted $(Boc)_2O$ from the reaction solution was washed with ethyl acetate and the pH of the aqueous layer was adjusted to 3 using citric acid, followed by extraction with ethyl acetate to obtain 18.9 g (96%) of N-Boc-L-serine as a transparent oily product.

Under ice cooling, 18.7 g of N-Boc-L-serine was dissolved in 200 ml of DMF and 13.25 g of solid $K_2CO_3$ was added and suspended for 15 minutes, and then 41.6 g (3.2 eq) of MeI was added, followed by stirring for 24 hours. After the reaction, the reaction solution was filtered through celite and concentrated. The residue was extracted by liquid separation using 400 ml of water and 150 ml×4 of ethyl acetate and dried over sodium sulfate. The ethyl acetate layer was concentrated and subjected to silica gel column chromatography to obtain 17.1 g (87.4%) of an N-Boc-L-serine methyl ester as a transparent oily product.

The obtained N-Boc-L-serine methyl ester (6.0 g) and 10.5 g (1.2 eq) of carbon tetrabromide were dissolved in 100 ml of dry THF and a solution prepared by dissolving 8.29 g (1.2 eq) of $Ph_3P$ in 50 ml of dry THF was added dropwise under ice cooling, followed by stirring at room temperature for 24 hours. After the reaction, the reaction solution was filtered and purified by silica gel column chromatography to obtain 4.9 g (65%) of methyl(S)-2-tert-butoxycarbonylaminopropanate as a white crystal.

Finally, 308 mg of methyl(S)-2-tert-butoxycarbonylamino-propanate was stirred overnight in 20 ml of 4N HCl at 60° C. and then concentrated to obtain 195 mg (90%) of (S)-2-amino-3-bromo-propionic acid hydrochloride.

(c) Preparation of Bromo Addition Norvaline in L-Form

This compound was prepared with reference to the method described in Tetrahedron: Asymmetry 9 (1998) 3381-3394.

L-glutamic acid (10 g) (1 eq) was dissolved in 90 ml of dry MeOH and 40.4 g (5 eq) of thionyl chloride was added dropwise over 30 minutes under an ice bath, followed by stirring overnight and further concentration. The residue was dissolved again in 150 ml of dry MeOH, and 44.7 g (6.5 eq) of $Et_3N$ and 16.3 g (1.1 eq) of $(Boc)_2O$ were added under an ice bath, followed by stirring for 6 hours. The reaction solution was concentrated and extracted by liquid separation using ethyl acetate, and then the organic layer was washed with 10% citric acid and washed with saturated NaHCO$_3$ and Brine. After drying over sodium sulfate, concentration and purification by silica gel column chromatography were performed, and 17.8 g (95%) of pale yellowish brown oily dimethyl(S)-2-tert-butoxycarbonylamino-pentanodioate was obtained.

Dimethyl(S)-2-tert-butoxycarbonylamino-pentanodioate (10 g) (1 eq) and 0.89 g (0.2 eq) of DMAP were dissolved in dry CH$_3$CN, and then 8.72 g (1.1 eq) of (Boc)$_2$O was added under an ice bath, followed by stirring overnight. After concentration, the reaction solution was purified by silica gel column chromatography to obtain 12.5 g (92%) of dimethyl (S)-2-{(tert-butoxy)-N-[(tert-butyl)oxy-carbonyl]carbonylamino}-1,5-pentanodioate as a white crystal.

Dimethyl(S)-2-{[tert-butoxy)-N-[(tert-butyl)oxy-carbonyl]carbonylamino}-1,5-pentanodioate (11 g) was dissolved in 290 ml of dry Et$_2$O and, after cooling to –78° C., 32 ml (1.1 eq) of diBAL-H (1 mol/l toluene solution) was added dropwise, followed by stirring for 5 minutes. Water (3.6 ml) (7 eq) was added, followed by stirring for 30 minutes, quenching, addition of sodium sulfate and further filtration with celite. After concentration, the residue was dissolved in about 100 ml of MeOH/THF and 1.1 g (1 eq) of NaBH$_4$ was added under ice cooling, followed by stirring for 2 hours. After concentration, the residue was purified by silica gel column chromatography to obtain 3.3 g (33%) of transparent oily methyl(S)-5-hydroxy-2-{(tert-butoxy)-N-[(tert-butyl)oxy-carbonyl]carbonylamino}-1-pentanoate.

Methyl(S)-5-hydroxy-2-{(tert-butoxy)-N-[(tert-butyl)oxy-carbonyl]carbonylamino}-1-pentanoate (3.2 g) and 4.58 g (1.5 eq) of carbon tetrabromide were dissolved in 30 ml of dry THF. Under ice cooling, a solution prepared by dissolving 3.62 g (1.5 eq) of Ph$_3$P in 10 ml of dry THF was added dropwise, followed by stirring for 24 hours. After filtration, the residue was purified by silica gel column chromatography to obtain 3.0 g (79%) of transparent oily methyl(S)-5-bromo-2-{(tert-butoxy)-N-(tert-butyl)oxy-carbonyl}carbonylamino]-1-pentanoate.

Finally, 2.33 g of methyl(S)-5-bromo-2-{(tert-butoxy)-N-[(tert-butyl)oxy-carbonyl]carbonylamino}-1-pentanoate was stirred in 50 ml of 4N HCl at 60° C. for 24 hours and then concentrated to obtain 1.29 g (98%) of (S)-2-amino-5-bromo-pentanoic acid hydrochloride.

(d) Preparation of Bromo Addition Aminooctanoic Acid in L-Form

This compound was prepared with reference to the method described in Tetrahedron Letters 45 (2004) 491-494.

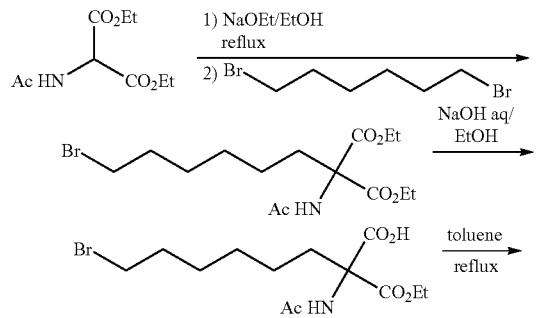

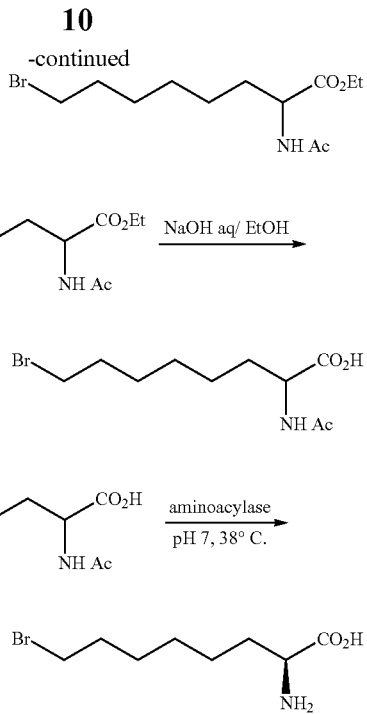

Diethylacetamide malonate (6.2 g) was dissolved in 29 ml of dry EtOH and 10.5 ml (0.95 eq) of 20% NaOEt was added dropwise, followed by stirring under reflux for 30 minutes, dropwise addition of 14.5 g (9 ml, 2 eq) of dibromohexane and further refluxing for 5 hours. While cooling under an ice bath, 5.7 ml (0.2 eq) of 1N NaOH was added dropwise every 15 minutes in the total amount of 28.6 ml (1 eq), followed by stirring overnight.

After concentration, the reaction solution was washed by liquid separation using diethylether. The pH of the aqueous layer was adjusted to about 3 using citric acid, followed by extraction with ethyl acetate. The ethyl acetate layer was washed with brine and dried over sodium sulfate. After concentration, the residue was stirred under reflux in 100 ml of toluene for 3 hours. After concentration, the residue was dissolved in ethyl acetate and insolubles were removed by filtration. The ethyl acetate layer was washed with saturated NaHCO$_3$ and brine and then dried over sodium sulfate. The ethyl acetate layer was concentrated to obtain 3.9 g (39%) of brown oily ethyl-2-(N-acetylamino)-5-bromooctanate.

Ethyl(S)-2-(N-acetylamino)-5-bromooctanate (3.9 g) was dissolved in EtOH and 12.7 ml (1 eq) of 1N NaOH was added every 1 hour in the total amount of 50.8 ml (4 eq), followed by stirring overnight. After concentration, the aqueous layer was washed by liquid separation using diethylether. The pH of the aqueous layer was adjusted to about 1 to 2 using 1N HCl, followed by extraction with diethylether. The diethylether layer was washed with brine and dehydrated over sodium sulfate. After concentration, 3.9 g (86.3%) of 2-(N-acetylamino)-5-bromooctanoic acid was obtained as a white solid.

To 2-(N-acetylamino)-5-bromooctanoic acid (3.0 g), 20 ml of water was added and 1N NaOH was added to adjust the pH to 8. After warming to 37° C., 400 mg of *Aspergillus* genus aminoacylaze was added, followed by stirring for 24 hours. After cooling in an ice bath, the obtained precipitate was collected by filtration. The product obtained by filtration was washed with water and ethanol until color disappeared. After drying, 658 mg (52%) of (S)-2-amino-5-bromooctanoic acid was obtained as a white crystal.

Example 1

Reaction of 2-amino-4-bromobutanoic acid in L-Form and cyanoethyl BSH

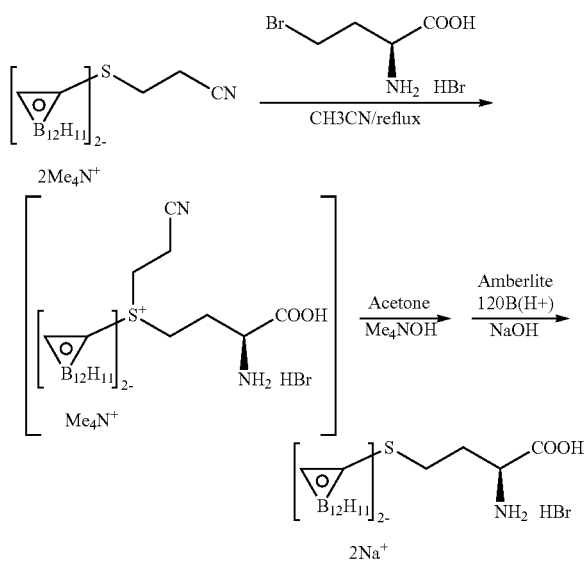

Boron 10-enriched $B_{12}H_{11}SCH_2CH_2CN \cdot 2TMA$ (2-cyanoethylthioundecahydrododecaborate ditetramethylammonium) 1 (500 mg, 1.0 eq.) was allowed to undergo azeotropy three times using 10 ml of anhydrous acetonitrile and then added to a 200 ml three-necked flask. A powdered 2-amino-4-bromobutanoic acid in L-form 7 (538 mg, 1.5 eq.) in a state where amino groups and carboxyl groups are not protected, and 50 ml of anhydrous acetonitrile were added, and the reaction solution was stirred under reflux in an inert gas using O/N. After the reaction, acetonitrile was distilled off and acetone was added, and then precipitated tetramethylammonium bromide was removed by filtration.

Next, a minimum amount of acetone (ca. 30 ml) was added at room temperature and 1.33 ml (1 eq) of a 10% methanol solution of tetramethylammonium hydroxide was added. The precipitated coarse crystal was collected by filtration, washed with acetone and then the unreacted 2-amino-4-bromobutanoic acid was removed by a cation-exchange resin. Recrystallization was performed from a water/acetone system to obtain a tetramethylammonium salt (349.1 mg, 52.1%) as a milky white crystal.

Finally, a tetramethylammonium salt was purely dissolved and passed through a cation-exchange resin AMBERLITE 1R 120B H+ type to remove tetramethylammonium ions, and then 16.9 mL (2 eq.) of 0.1 N sodium hydroxide was added, followed by concentration to obtain a sodium salt (249.4 mg, 95.1%) as a brown oily product.

$^1$H NMR (400 MHz, $D_2O$): 0.75-1.65 (11H, br, B12H11), 1.72 and 1.86 (2H, m, C$\underline{H}$2CH(NH2)COOH), 2.48 (2H, m, C$\underline{H}$2CH2CH(NH2)COO$\underline{H}$), 3.22 (1H, m, C$\underline{H}$(NH2)COOH)

Example 2

In the same manner as in Example 1, except that bromo addition alanine in L-form was used in place of 2-amino-4-bromobutanoic acid in L-form, BSH-alanine in L-form was obtained (yield: 21.4%).

$^1$H NMR (400 MHz, $D_2O$): 0.60-1.70 (11H, br, B12H11), 1.13 (2H, m, C$\underline{H}$2CH(NH2)COOH), 3.49 (1H, m, C$\underline{H}$(NH2)COOH)

Example 3

In the same manner as in Example 1, except that bromo addition norvaline in L-form was used in place of 2-amino-4-bromobutanoic acid in L-form, BSH-norvaline in L-form was obtained (yield: 78%).

$^1$H NMR (400 MHz, $D_2O$): 0.65-1.70 (11H, br, B12H11), 1.40-1.55 (4H, m, CH2C$\underline{H}$2CH(NH2)COOH), 2.36 (2$\underline{H}$, m, C$\underline{H}$2CH2CH(N$\underline{H}$2)COOH), 3.25 (1H, m, C$\underline{H}$($\overline{N}$H2)COOH)

Example 4

In the same manner as in Example 1, except that bromo addition aminooctanoic acid in L-form was used in place of 2-amino-4-bromobutanoic acid in L-form, BSH-aminooctanoic acid in L-form was obtained (yield: 65%).

$^1$H NMR (400 MHz, $D_2O$): 0.50-1.70 (11H, br, B12H11), 1.16 (6H, m, CH2C$\underline{H}$2CH2C$\underline{H}$2CH(NH2)COOH), 1.39 (4H, m, CH2CH2C$\underline{H}$2C$\underline{H}$2CH(NH2)COOH), 2.34 (2H, t, J=7.1 Hz, CH2CH2C$\underline{H}$2CH2CH2CH2CH(NH2)COOH), 3.07 (1H, t, J=6.0 Hz, C$\underline{H}$(NH2)COOH)

Example 5

In the same manner as in Example 1, except that a protected amino acid in which amino groups and carboxyl groups were respectively protected with acetyl groups and methyl groups in accordance with a conventional method was used in place of the 2-amino-4-bromobutanoic acid in L-form of Example 1, the reaction was similarly performed.

In detail, first, cyanoethyl BSH (200 mg, 1.0 eq.) and a protected amino acid (198 mg, 1.5 eq) were respectively allowed to undergo azeotropy using anhydrous acetonitrile several times and then added in a 50 ml two-necked flask.

Next, stirring was performed under reflux in an inert gas using anhydrous acetonitrile in the total amount of 15 ml for 19 hours. The precipitated tetramethylammonium bromide was removed by filtration. The filtrate was concentrated under reduced pressure and dissolved in pure water, and then the unreacted protected amino acid was washed with diethylether. The aqueous layer was concentrated under reduced pressure and recrystallized from hot water to obtain a brown solid (231 mg, 90.7%).

Into a 100 ml volume recovery flask, the obtained brown solid (23 mg) was charged and dissolved by adding a minimum amount of acetone (ca. 30 ml) at room temperature. To the solution, 0.56 ml (1 eq) of a 10% methanol solution of tetramethylammonium hydroxide was added. The precipitated coarse crystal was filtered and washed with acetone to obtain a milky white crystal (218 mg, 88.7%).

Next, into 50 ml volume recovery flask, the obtained crystal (50 mg) was charged and suspended in 2 ml of MeOH, and then 0.13 ml of 1N NaOH was added. The crystal was dissolved by adding a minimum amount of pure water. After confirming disappearance of the raw material on TLC, the solution was concentrated under reduced pressure and dissolved in pure water and then passed through a cation-exchange resin AMBERLITE 1R 120B H+ type.

Finally, 2.08 ml (2 eq) of a 0.1N NaOH solution was added and the solution was concentrated under reduced pressure to obtain a transparent oily product (36.6 mg, 96.8%). To a 50 ml volume recovery flask, this oily product (34 mg) and 5 ml of 6N NaOH were added, followed by stirring at 80° C. for 3 days. After passing through a cation-exchange resin AMBERLITE 1R 120B H+ type, a white solid concentrated under reduced pressure was washed with hexane. After dissolving in water, 0.98 ml (2 eq) of a 0.1N NaOH solution was added. The solution was concentrated under reduced pressure to obtain a final BSH amino acid in L-form (15.6 mg, 52%) as a transparent oily product.

$^1$H NMR (400 MHz, D$_2$O): 0.70-1.62 (11H, br, B12H11), 1.70 and 1.81 (2H, m, CH2CH(NH2)COOH), 2.45 (2H, m, CH2CH2CH(NH2)COOH), 3.20 (1H, m, CH(NH2)COOH)

The invention claimed is:

1. A method for producing an optically active BSH amino acid, comprising the step of reacting an optically active α-amino acid derivative having a halogen in a side chain with a cyanoethyl BSH compound represented by the formula:

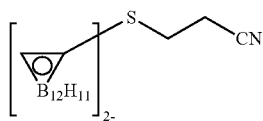
(1)

wherein said amino acid derivative is represented by the structural formula:

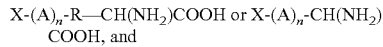

X-(A)$_n$-R—CH(NH$_2$)COOH or X-(A)$_n$-CH(NH$_2$)COOH, and a coupling manner of an amino group or carboxyl group to α carbon is optical isomers sterically in D-form or L-form, while X represents one halogen atom selected from the group consisting of a chlorine atom, a bromine atom, an iodine atom, and a fluorine atom, A represent a linear alkylene, a branched alkylene or a substituted alkylene, n represents an integer of from 1 to 10, and R represents a linear alkylene, branched alkylene, or substituted alkylene having 1 to 6 carbon atom.

2. The method according to claim 1, wherein the halogen is bromine.

3. The method according to claim 1, wherein the optically active BSH amino acid is in L-form.

4. The optically active BSH amino acid according, which is a compound represented by the formula:

[Formula 2]

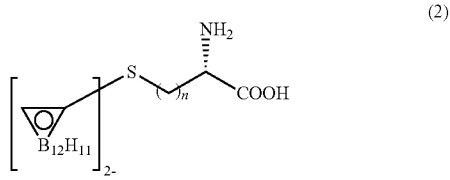
(2)

wherein n represents an integer of from 1 to 6, or a pharmaceutically acceptable salt thereof which optically active BSH amino acid is obtained by a method comprising the step of reacting an optically active α-amino acid derivative having a halogen in a side chain with a cyanoethyl BSH compound represented by the formula:

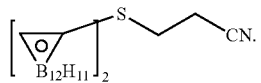

* * * * *

UNITED STATES PATENT AND TRADEMARK OFFICE
CERTIFICATE OF CORRECTION

PATENT NO. : 8,431,738 B2
APPLICATION NO. : 13/055700
DATED : April 30, 2013
INVENTOR(S) : Kirihata et al.

It is certified that error appears in the above-identified patent and that said Letters Patent is hereby corrected as shown below:

Title Page (item 57, Abstract) line 4, Change "a-amino" to --α-amino--.

In the Specification
Column 6, line 18, Change "like" to --like.--.
Column 8, lines 48-49, Change "-butoxycarbonylaminopropanate" to
-- -butoxycarbonylaminopropanoate--.
Column 8, lines 50-51, Change "-butoxycarbonylamino-propanate" to
-- -butoxycarbonylaminopropanoate--.
Column 9, line 6, Change "-pentanodioate" to -- -pentanedioate--.
Column 9, line 8, Change "-pentanodioate" to -- -pentanedioate--.
Column 9, line 16, Change "-pentanodioate" to -- -pentanedioate--.
Column 9, line 18, Change "-pentanodioate" to -- -pentanedioate--.

In the Claims
Column 14, line 8, Claim 4, Change "amino acid according, which" to --amino acid, which--.

Signed and Sealed this
Fifth Day of November, 2013

Teresa Stanek Rea
*Deputy Director of the United States Patent and Trademark Office*